United States Patent [19]

Nanjin et al.

[11] Patent Number: 5,275,817
[45] Date of Patent: Jan. 4, 1994

[54] PHYSIOLOGICALLY ACTIVE KANGLEMYCIN C

[75] Inventors: Wang Nanjin; Yang Xianshu, both of Beijing, China

[73] Assignee: Nippon Kayaku Kabushiki Kaisha, Tokyo, Japan

[21] Appl. No.: 839,614

[22] Filed: Feb. 21, 1992

[30] Foreign Application Priority Data

Mar. 1, 1991 [CN] China ............................. 91101127.7

[51] Int. Cl.$^5$ ............................................ A61K 35/74
[52] U.S. Cl. ..................................... 424/122; 435/169
[58] Field of Search ......................... 424/122; 435/169

Primary Examiner—Jerome D. Goldberg
Attorney, Agent, or Firm—Nields & Lemack

[57] ABSTRACT

Novel physiologically active substance, kanglemycin C, having a molecular weight of 326 and is isolated from the fermentation broth of *Nocardia mediterranei var. kanulensis* 1747-64 which belongs to the genus Nocardia. Kanglemycin C has an immunosuppressive activity and inhibits proliferation of tumor cells in vitro.

1 Claim, 4 Drawing Sheets

PHYSIOLOGICALLY ACTIVE KANGLEMYCIN C

BACKGROUND OF THE INVENTION

1. Field of the Invention

The present invention relates to kanglemycin C which is a physiologically active substance. More particularly, the present invention relates to kanglemycin C which is used as a novel immunosuppressant for the treatment of autoimmune hemolytic anemia, nephritis as well as the rejection of connecting tissue and viscera transplantation.

2. Related Art Statement

Immunosuppressants recently developed as having high selectivity possess an activity of specifically regulating the subgroup of a certain immune cell. Cyclosporin A which is a representative of such immunosuppressants selectively inhibits the proliferation of helper T cell clone and has thus achieved a remarkable result in the field of organ transplantation. With the achievement, cyclosporin A (Agents and Actions, 1976, Vol 6, 468-475) has been widely used in the clinic. However, cyclosporin A is accompanied by side effects such as acute (or chronic) renal intoxication, mild tremor, neural lesion, gingiva pachismus, loss of hair, etc.

FK-506 (Journal of Antibiotics, Vol 40, 1249 (1987)) which was found recently is a macrolide antibiotic ($C_{44}H_{69}NO_{22}$) and has proven favorable results on an experimental level. However, due to its complicated process, it is likely that clinical application of this drug to the clinic might be limited.

SUMMARY OF THE INVENTION

Accordingly, an object of the present invention is to provide a more ideal immunosuppressant which can overcome various drawbacks of conventional immunosuppressants.

The present inventors have made extensive studies aiming at obtaining a novel immunosuppressant which can eliminate the disadvantages involved in known immunosuppressants. As a result, kanglemycin C having an extremely small molecular weight which is a new immunosuppressant was obtained from the fermentation broth of a strain belonging to the genus Nocardia, which has been changed to Amycolatopsis (International Journal of Systematic Bacteology, Jan. 1986, p. 29-37), and it has been found that this novel immunosuppressant having better properties could be an immunosuppressant in coming generation. The present invention has thus been attained.

The present invention provides, in the first aspect, physiologically active kanglemycin C and pharmaceutical acceptable salts thereof characterized by the following physicochemical properties and salts thereof.

(1) Molecular weight (EI-MS): m/z 326 (M+)
(2) Molecular formula: $C_{19}H_{18}O_5$
(3) Melting point: 170° C. (dec.)
(4) Optical rotation: $[\alpha]_D^{25} + 150°$ (C. 0.57, MeOH)
(5) UV absorption spectrum (MeOH): $\lambda_{max}^{nm}$ (log ε) 232 (4.61), 356 (3.93)
(6) IR absorption spectrum (KBr) (cm$^{-1}$): 3400, 1690, 1650, 1640
(7) $^{13}$C-NMR (100 MHz, DMSO-d$_6$): 204.02 (s), 160.58 (s), 70.92 (s), 20.47 (t), 195.0 (s), 159.50 (s), 136.66 (d), 134.58 (s), 43.62 (d), 23.75 (q), 123.95 (d), 46.52 (t), 31.47 (t), 44.89 (d), 117.69 (s), 122.68 (d), 118.21 (d), 196.90 (s), 54.93 (d)
(8) $^1$H-NMR (400 MHz, DMSO-d$_6$) 5.78 (1H, brs), 1.98 (3H, s), 2.79 (1H, d, J=18.54), 2.35 (1H, d, J=18.54), 1.47 (2H, m), 1.98 (1H, m), 1.79 (1H, m), 1.98 (1H, t), 7.30 (1H, d), 7.75 (1H, t), 7.55 (1H, d), 2.91 (1H, d), 3.37 (1H, d)

DETAILED DESCRIPTION OF THE INVENTION

Figure 1:
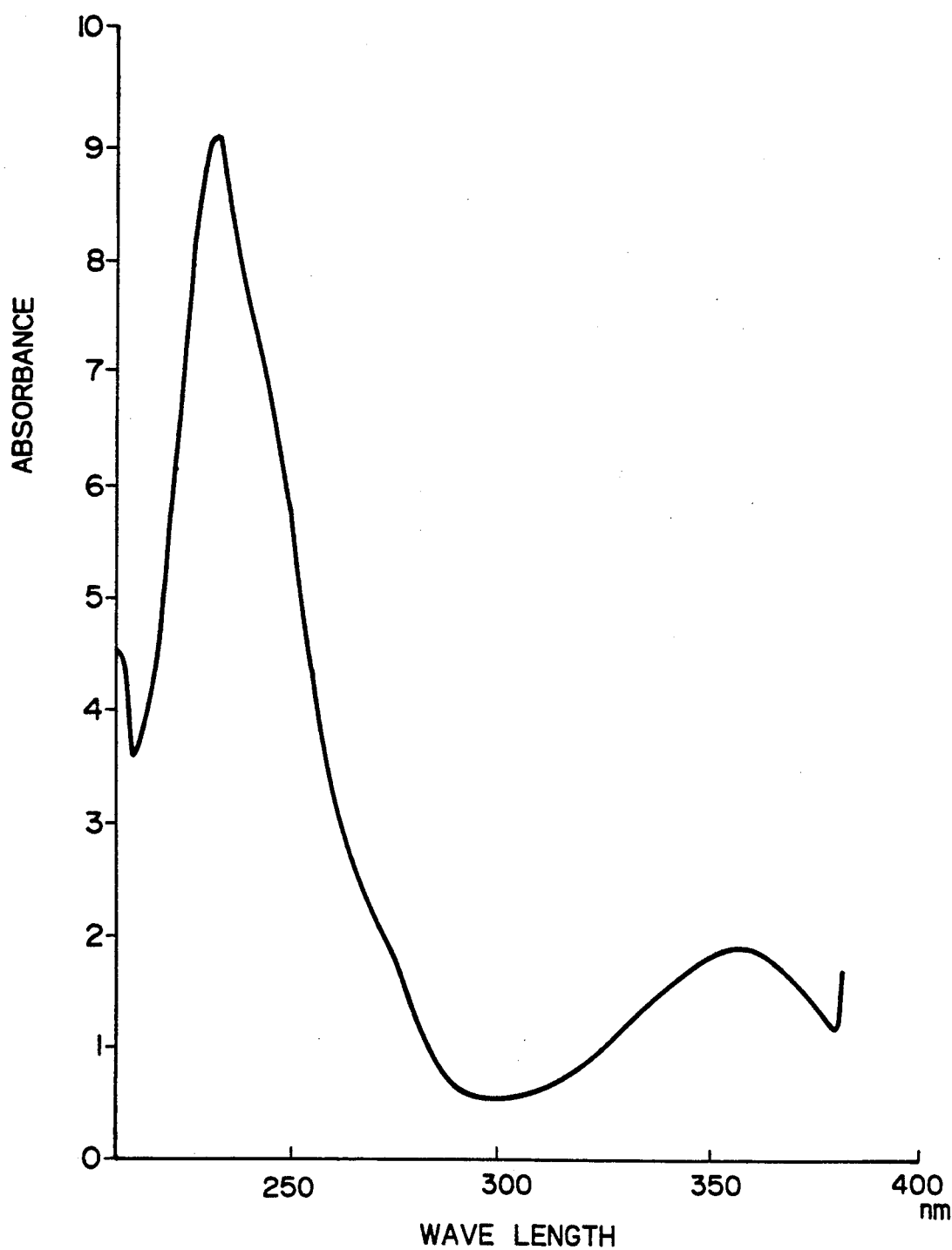
FIG. 1 shows UV absorption spectrum of kanglemycin C.

Kanglemycin C of the present invention has a molecular weight of 326 as is noted from the physicochemical properties described above, which is extremely small as compared to the molecular weight of known immunosuppressants.

Its optical rotation is:

$$[\alpha]_D^{25} + 150° \text{ (C 0.57, MeOH)}$$

Kanglemycin C in methanol shows the maximum absorption at 232 nm and 356 nm in UV absorption spectrum; shows absorption at 3400 cm$^{-1}$, 1690 cm$^{-1}$, 1650 cm$^{-1}$, 1640 cm$^{-1}$, 750 cm$^{-1}$, etc., in IR absorption spectrum. The molecular formula ($C_{19}H_{18}O_5$) determined from the elemental analysis. This compound is soluble in a polar organic solvent but insoluble in water and a non-polar organic solvent. Purified kanglemycin C is a yellowish needle.

The physiologically active kanglemycin C of the present invention can be obtained by culturing a kanglemycin C-producing microorganism belonging to the genus Nocardia, producing and accumulating kanglemycin C and harvesting kanglemycin C from the thus obtained fermentation broth.

A representative example of the microorganism capable of producing kanglemycin C is *Nocardia mediterranei var. kanqlensis* 1747-64 which belongs to the genus Nocardia and was harvested in the people's Republic of China. Bacteriological properties and physiological properties, etc. of this strain are given below.

1. Morphological property

The strain was observed after incubation at 28° C. for 2 weeks. Hyphae are simple with flexous or loop periphery. Fragmentation of substrate mycelium is observed. Neither sporangium nor whorl is formed. The spore surface is smooth or rough and sometimes spiny. Spores are cylindrical and have a size of 0.6−0.8×0.8 −1.3 μm. About 10 chains are gathered to form a spore.

2. Growth in various media

The growth state at 28° C. in various media observed 2 weeks after is shown in Table 1 below.

TABLE 1

| Medium | Growth | Aerial Mycelium | Substrate Mycelium | Soluble Pigment |
|---|---|---|---|---|
| Sucrose-nitrate agar medium | Good | Moderate, white to light yellow | Light yellow to light orange | Brownish |

TABLE 1-continued

| Medium | Growth | Aerial Mycelium | Substrate Mycelium | Soluble Pigment |
|---|---|---|---|---|
| Glucose-asparagine agar medium | Moderate | Moderate, white to light yellow orange | Light yellow to light orange | Yellowish |
| Glycerin-asparagine agar medium | Good | Moderate, white to light yellow orange | Light yellow to light orange | Brown |
| Starch-inorganic salts agar medium | Moderate | Moderate, white | Light yellow to light yellow brown | Brownish |
| Tyrosine-agar medium | Moderate | Moderate, white | Light yellow to light yellow brown | Brownish |
| Nutrient agar medium | Moderate | Moderate, white to light yellow orange | Light yellow to light orange | None |
| Yeast-malt agar medium | Moderate | Moderate, white | Light brown | Yellowish |
| Oatmeal agar medium | Moderate | Moderate, pale orange to light yellow brown | Pale orange | Yellowish |
| Peptone-yeast iron agar medium | Moderate | — | Light yellow | None |

3. Physiological property

Optimum growth temperature: 27°–37° C.
Reduction of nitrate: negative
Liquefaction of gelatin (glucose-peptone-gelatin medium, 20° C.): negative
Hydrolysis of starch (starch-inorganic salts agar medium): negative
Coagulation of skimmed milk: positive
Peptonization of skimmed milk: positive
Formation of melanoide pigment: negative 4. Utilization of carbon sources
(Pridham-Gottliebagar medium)

| | |
|---|---|
| L-Arabinose | + |
| D-Xylose | + |
| D-Glucose | + |
| D-Fructose | + |
| Sucrose | + |
| Inositol | + |
| L-Rhamnose | + |
| Raffinose | − |
| D-Mannitol | + |

5. Diaminopimelic acid in cell wall
meso-Diaminopimelic acid

In summary, the cell wall of this strain is meso-diaminopimelic acid. According to the method of International Streptomyces Project (abbreviated as ISP); spore-forming hyphae belong to the section: Rectiflexibles or Recticuliaperti; the spore surface is smooth or rough; the color of mature hypha is white color series; the strain does not form melanaide pigments or any pigment in medium; the color of substrate mycelium is light brown or light yellow; division is noted; the strain grows by utilizing carbon sources such as L-arabinose, D-glucose, D-fructose, sucrose, inositol, L-rhamnose, D-xylose and D-mannitol but does not utilize raffinose.

Based on the foregoing properties, bacteriological survey was conducted following Bergey's Manual of Determinative Bacteriology, 8th edition (1974); the results reveal that the strain belongs to the genus Nocardia. Therefore, the strain was named *Nocardia mediterranei var. kanglensis* 1747-64 (hereinafter referred to as strain 1747-64). The strain was deposited in the Committee of Preservation and Control of Chinese Microorganism in the People's of Republic of China on Feb. 20, 1991 and was given Accession No. CGMCC No. 0163. This strain was also deposited in the Fermentation Research Institute of the Agency of Industrial Science & Technology of Japan, 1-3, Higaski 1 Chome Tsukuba-shi Ibarski-Ken 305, Japan, on Jan. 28, 1992 under the Budapest Treaty, and was given Accession No. FERM BP-3718.

Kanglemycin C of the present invention can be prepared by culturing a kanglemycin C-producing microorganism belonging to the genus Nocardia and harvesting the physiologically active kanglemycin C from the fermentation broth.

As the medium for culturing the kanglemycin C-producing bacteria, any medium may be used so long as it contains appropriate nutrient sources the kanglemycin C-producing bacteria can assimilate. As the carbon sources, there may be utilized, for example, glycerin, glucose, maltose, sucrose, dextrin, starch, oils and fats, etc. As the nitrogen sources, there may be utilized organic materials such as soybean meal, cotton seed meal, meat extract, peptone, dry yeast, yeast seed meal, meat extract, peptone, dry yeast, yeast extract, corn steep liquor, etc.; inorganic materials such as ammonium nitrate, ammonium sulfate, sodium nitrate, calcium carbonate, ammonium chloride, etc.

If necessary and desired, inorganic salts such as sodium chloride, potassium chloride, malates, heavy metal salts, etc., and aminoacids, vitamins may also be supplemented.

In order to prevent foaming during fermentation, appropriate defoaming agents, e.g., silicone, soybean oil, etc. may also be suitably added in a conventional manner.

For the cultivation, deep aerial spinner culture is the most preferred method, as is conventionally adopted to produce antibiotics.

The culture temperature is not particularly limited as long as kanglemycin C can be produced at the temperature, for example, in the range of 25 to 37 without substantially preventing growth of the kanglemycin C-producing bacteria. A particularly preferred temperature is in the range of 27° to 32° C.

The cultivation is continued generally until kanglemycin C is sufficiently accumulated. The time period for the cultivation varies depending upon composition of medium and temperature for incubation. In general, the desired kanglemycin C can be obtained by culturing for 20 to 60 hours.

In more detail, cultivation may be performed as shown in Example 1 hereinafter. That is, the 1747-64 strain is subjected to slant culture in a slant culture medium composed of starch, sodium chloride, potassium nitrate, agar, etc. Then, the cake of mycelium is collected from the slant culture medium and inoculated on a seed culture medium. The seed culture medium is composed of glucose, yeast extract, soybean lees, potassium hydrogenphosphate, ammonium sulfate, etc. Incubation is continued in the seed culture medium at 25° to 32° C. for 24 to 55 hours. Then, the thus obtained seed fermentation broth is transferred to a fermentation medium followed by culturing at 25° to 32° C. for 68 to 96 hours. The fermentation medium is composed of glucose, yeast extract, soybean meal, peptone, calcium carbonate, etc. From the thus obtained fermentation broth, kanglemycin C can be harvested.

To isolate kanglemycin C from the thus obtained fermentation broth, an appropriate method may be used suitably.

For example, the fermentation broth is filtered and the mycelium are removed by known methods for isolation, e.g., centrifugation. From the supernatant, kanglemycin C can be isolated, purified and harvested by solvent extraction using an appropriate solvent, chromatography utilizing adsorption or ion exchange ability, singly or in combination.

The kanglemycin C of the present invention has an activity of strongly inhibiting immune cells, especially conversion of spleen cells. According to the present invention, there is provided an immunosuppressant comprising as an effective ingredient kanglemycin C or pharmaceutically acceptable salts thereof. The immunosuppressant of the present invention may be administered to warm-blooded animal including human in an effective dose of kanglemycin C. The immunosuppressant may be injected parenterally; alternatively, the immunosuppressant may also be orally administered or by parenteral route other than injection. Dose of kanglemycin C may vary depending upon the subject to the administered or route for administration but is generally in the range of 0.1 mg to 100 mg/kg/day, preferably 0.5 to 50 mg/kg/day.

Pharmaceutical preparations are not particularly limited. Kanglemycin C is prepared into a liquid or solid preparation containing 0.01 to 50 wt% of kanglemycin C, based on the total weight of the preparation, together with pharmaceutical additives conventionally used, for example, carriers, auxiliary agents, etc. The preparation is administered orally or parenterally.

As is appreciated from the foregoing description, kanglemycin C which is a novel physiologically active substance can be obtained from the fermentation broth of strain 1747-64 belonging to the genus Nocardia. Kanglemycin C strongly inhibits the conversion of immune cells, especially spleen cells and strongly inhibits proliferation of tumor cells Furthermore, kanglemycin C can be advantageously prepared from an industrial viewpoint because of its extremely small molecular weight as compared to known immunosuppressants.

Therefore, kanglemycin C can be expected as a promising immunosuppressant of the next generation, since kanglemycin C can eliminate various disadvantages encountered with known immunosuppressants.

Hereafter the present invention is described in more detail, with reference to the examples and test examples.

EXAMPLE 1

Production of kanglemycin C

The 1747-64 strain was cultured and fermented. The thus obtained fermentation broth was extracted with an organic solvent. Kanglemycin C was isolated and purified from the extract by column chromatography. Detailed conditions are shown below.

(1) Slant culture medium (%): $KNO_3$ 0.1, NaCl 0.5, $K_2HPO_4$ 0.05 $FeSO_4$ 0.01, starch 2, agar 1.7, cold boiled water, pH 7.0, incubation at 28° C. for 5-7 days;

(2) Seed culture medium (%): glucose 2.5, yeast powder 0.5, KCl 0.25, soybean meal 0.5, $K_2HPO_4$ 0.02 $(NH_4)_2SO_4$ 0.5, $MgSO_4$ 0.02, $CaCO_4$ 0.5, tap water 100 ml, (pH not adjusted);

(3) Composition of fermentation medium (%): -glucose 3, yeast extract powder 1, soybean meal 0.5, peptone 0.2, $CaCO_3$ 0.1, tap water 100 ml (pH not adjusted)

The media described above were all sterilized at 121° C. for 30 minutes in an autoclave and reserved for use. A loop of slant culture of strain 1747-64 was inoculated on a shake flask of 250 ml volume charged with 50 ml of seed culture medium and then cultured at 28° C. for 48 hours in a rotary shaker (180–200 rpm). The thus obtained seed culture broth was transferred to a shake flask of 500 ml volume containing 50 ml of fermentation medium in a proportion of 10% (by volume). After culturing at 28° C. for 72 hours in a rotary shaker (180–200 rpm), the fermentation broth was obtained.

Figure 2:
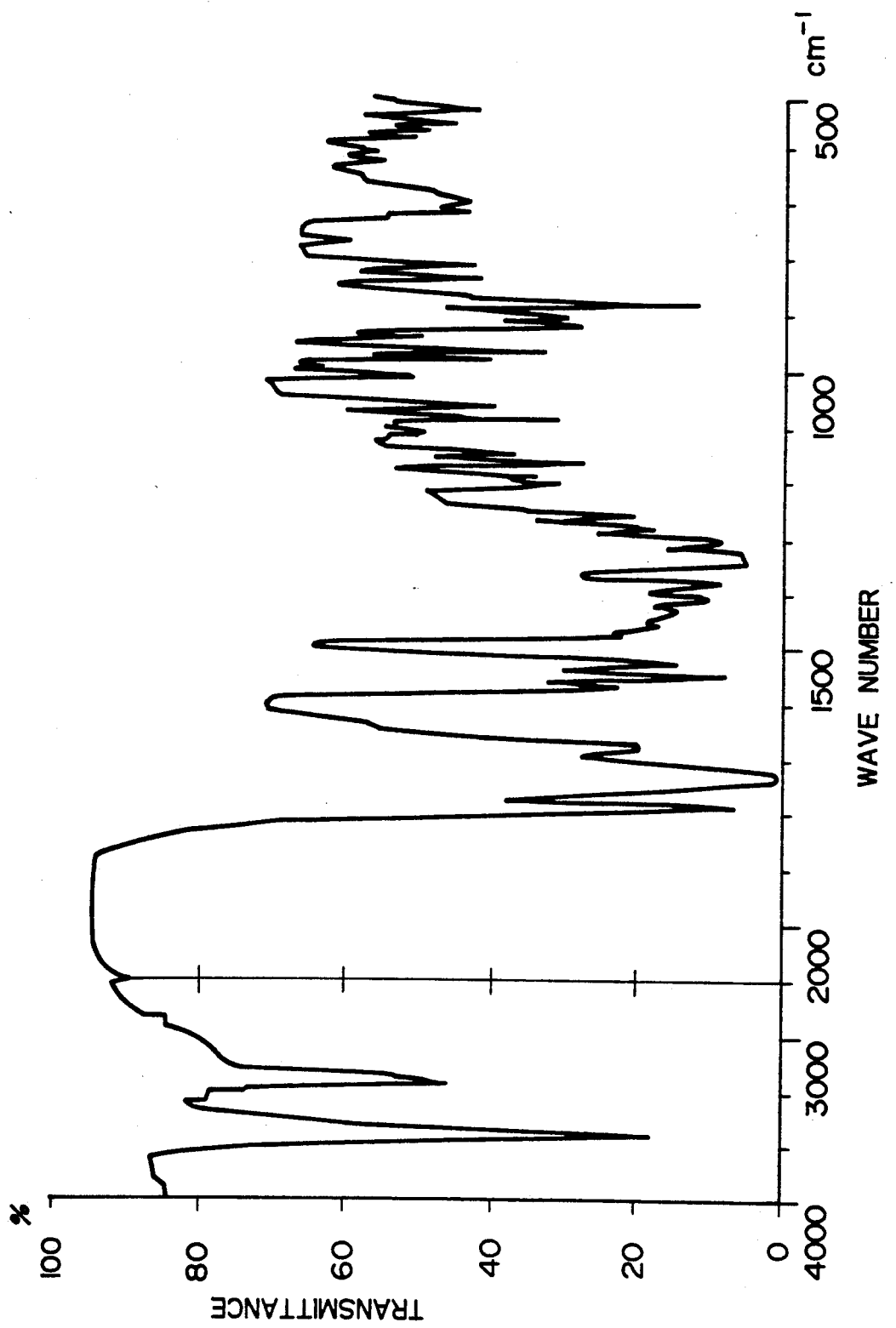
FIG. 2 shows IR absorption spectrum (KBr) of kanglemycin C.

The fermentation broth was filtered and the filtrate was adjusted to pH 4 with an inorganic acid. The filtrate was extracted with butyl acetate. After the extract was concentrated, the concentrate was subjected to silica gel chromatography. After eluting with a mixture of chloroform and methanol (30 : 1), the active fractions in the eluate were collected and concentrated. The concentrate was further purified on Sephadex TM LH-20 column with ethanol. The active fractions eluted with ethanol were collected and concentrated. Recrystallization from ethanol gave purified kanglemycin C. Kanglemycin C. is yellowish needles and decomposes at 170° C. The molecular weight of this substance is 326 and its optical rotation is:

$$[\alpha]_D^{25} + 150° \text{ (c 0.57, MeOH)};$$

the maximum UV absorption spectrum in methanol are observed at 232 nm and 256 nm (see FIG. 1); IR absorption spectrum are noted at 3400 $cm^{-1}$, 1690 $cm^{-1}$, 1650 $cm^{-1}$, 1640 $cm^{-1}$, 750 $cm^{-1}$ (see FIG. 2). This compound is soluble in a polar organic solvent but insoluble in water and a non-polar organic solvent.

EXAMPLE 2

Isolation and purification of kanglemycin C

To 33 l of the fermentation broth obtained in a manner similar to Example 1 was added 20 l of butyl acetate. The pH of the mixture was adjusted to 4.0 with 3 N hydrochloric acid and extracted. The organic phase was evaporated off to dryness under reduced pressure to obtain 3.12 g of the residue. The residue was dissolved in 30 ml of methanol and 30 g of silica gel (manufactured by Chingtao Kaiyo Kako Factory) was added to the solution. The mixture was evaporated off to dryness under reduced pressure. The residue was laid on a 800 ml of silica gel column packed with chloroform. The column was developed with chloroform-methanol (30 : 1) and the desired fractions were collected. Thus, 25.3 mg of brownish powder was obtained. The powder was dissolved in ethanol. The solution was passed through a column of ml Sephadex LH-20 (trademark, manufactured by Pharmacia Fine Chemicals Inc.)

packed with ethanol, which was then developed with ethanol. The desired fractions were collected and evaporated to dryness under reduced pressure. The residue was recrystallized from a small amount of ethanol to obtain 9.5 mg of kanglemycin C. as yellowish needles.

Melting point: 170° C. (dec.) EI-MS m/z: 326 (M+)
Elemental analysis: ($C_{19}H_{18}O_5$)
Calcd.: C. 69.93, H 5.55
Found: C. 69.58, H 5.60

Figure 3:
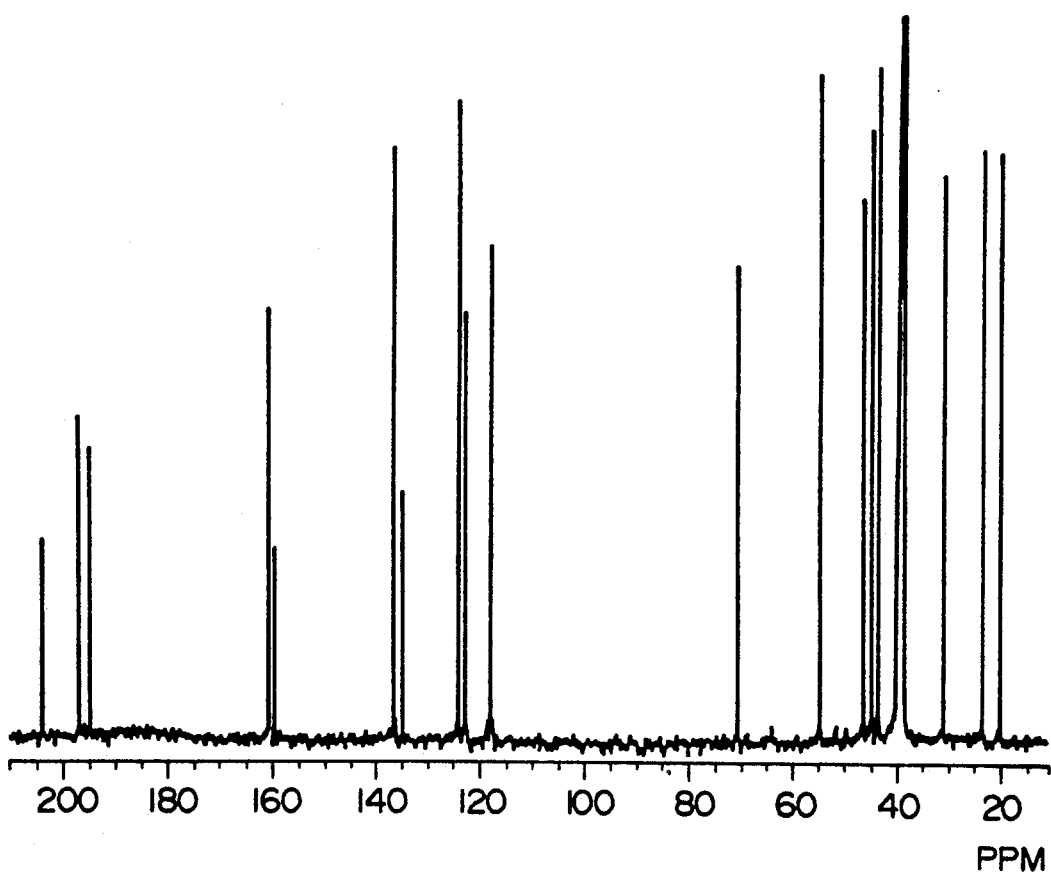
FIG. 3 shows $^{13}$C-NMR spectrum (100 MHz, DMSO-d$_6$) of kanglemycin C.
Figure 4:
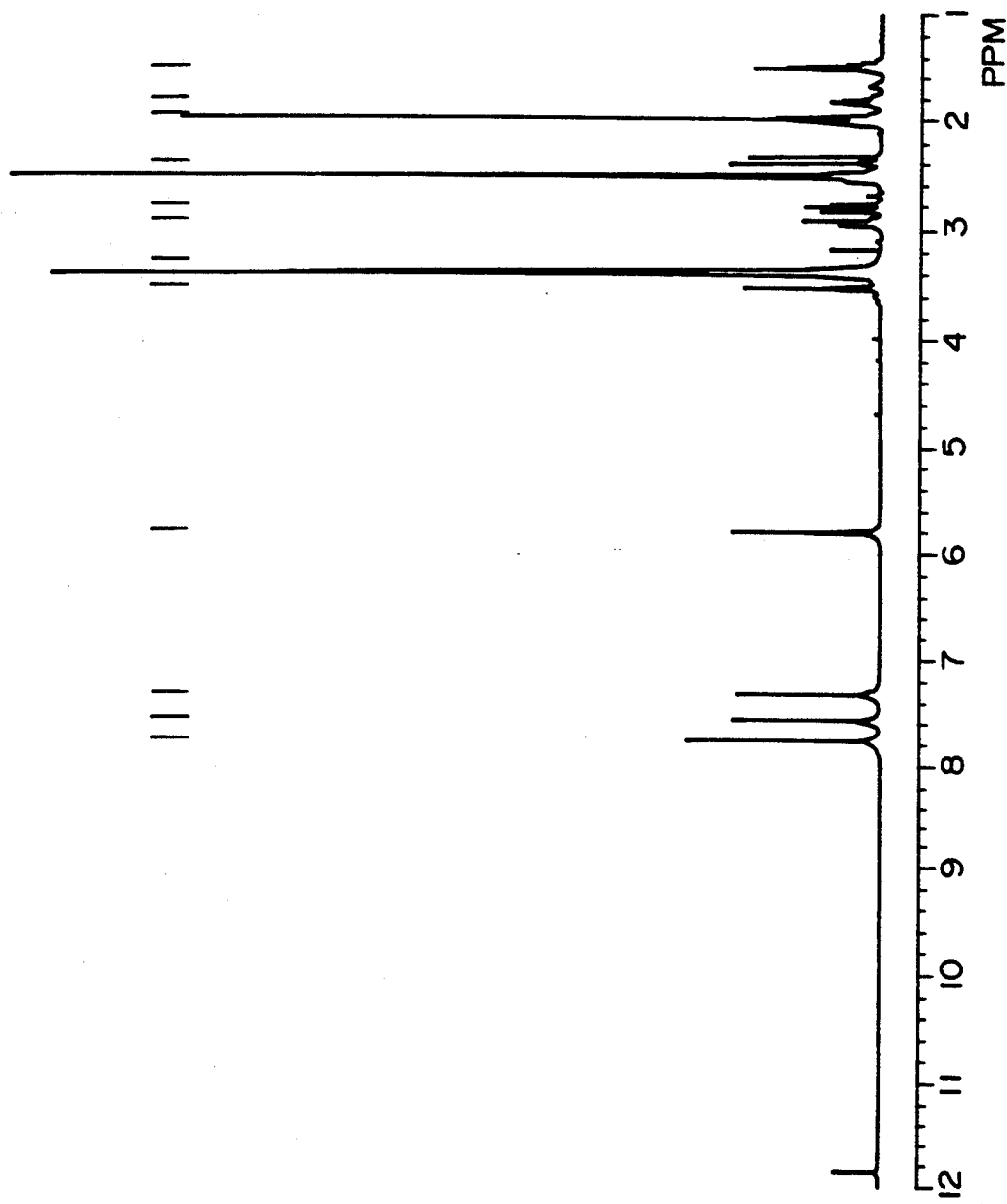
FIG. 4 shows $^1$H-NMR spectrum (400 MHz, DMSO-d$_6$) of kanglemycin C.

$^{13}$C-NMR (100 MHz, DMSO-$d_6$) (see FIG. 3): 204.02 (s), 160.58 (s), 70.92 (s), 20.47 (t), 195.0 (s), 159.50 (s), 136.66 (d), 134.58 (s), 43.62 (d), 23.75 (q), 123.95 (d), 46.52 (t), 31.47 (t), 44.89 (d), 117.69 (s), 122.68 (d), 118.21 (d), 196.90 (s), 54.93 (d)

$^1$H-NMR (400 MHz, DMSO-$d_6$) 5.78 (1H, brs), 1.98 (3H, s), 2.79 (1H, d, J=18.54), 2.35 (1H, d, J=18.54), 1.47 (2H, m), 1.98 (1H, m), 1.79 (1H, m), 1.98 (1H, t), 7.30 (1H, d), 7.75 (1H, t), 7.55 (1H, d), 2.91 (1H, d), 3.37 (1H, d)

HPLC: Column: Senshu Pak ODS-2151-A 6$\phi$×150 mm
Temperature: 35° C.
Detection: UV (232 nm)
Mobile phase: $CH_3CN$: 0.1 M phosphate buffer (pH 6.0)=4:6
Retention time: 7.41 minutes (kanglemycin C)

TEST EXAMPLE

Immunosuppressing activity and tumor cell growth inhibitory activity of kanglemycin C and toxicity By administering kanglemycin C. in a dose of 0.5 μg/ml, the inhibition rate against conversion of mouse spleen lymphocyte reached 96.9%. When mouse spleen cells were cultured, kanglemycin C did not show toxicity in a dose of 40 μg/ml, indicating that there is no toxicity on spermatogenous cells in a concentration of 1 mg/ml.

Even when kanglemycin C was intravenously administered to mouse in a dose of 2 mg/kg, no death was noted. It was thus confirmed that the toxicity is very low.

Kanglemycin C inhibited proliferation of K562 leukemia cells in a concentration of 0.1 μg/ml or less and inhibited proliferation of HeLa $S_3$ cells in a concentration of 0.1 μg/ml.

EXAMPLE 3

Preparation of tablet

A mixture of 30 parts by weight of klanglemycin C, 120 parts by weight of crystalline lactose, 147 parts by weight of crystalline cellulose and 3 parts by weight of magnesium stearate was tableted using a v-shaped blending machine to obtain a tablet of 300 mg.

What is claimed is:

1. Kanglemycin C which is a physiologically active substance, having the following physiocochemical properties or a pharmaceutically acceptable salt thereof:
   (1) Molecular weight (EI-MS): m/z 326 (M+)
   (2) Molecular formula: $C_{19}H_{18}O_5$
   (3) Melting point: 170° C. (dec.)
   (4) Optical rotations: $[\alpha]_D^{25}$ +150° (c 0.57, MeOH)
   (5) UV absorption spectrum (MeOH): $\lambda_{max}^{nm}$ (log $\epsilon$) 232 (4.61), 356 (3.93)
   (6) IR absorption spectrum (KB) (cm$^{-1}$): 3400, 1690, 1650, 1640
   (7) $^{13}$C-NMR (100 MHz, DMSO-$d_6$): 204.02 (s), 160.58 (s), 70.92 (s), 20.47 (t), 195.0 (s), 159.50 (s), 136.66 (d), 134.58 (s), 43.62 (d), 23.75 (q), 123.95 (d), 46.52 (t), 31.47 (t), 44.89 (d), 117.69 (s), 122.68 (d), 118.21 (d), 196.90 (s), 54.93 (d).
   (8) $^1$H-NMR (400 MHz, DMSO-$d_6$) 5.78 ($^1$H, brs), 1.98 (3H, s), 2.79 (1H, d, J=18.54), 2.35 (1H, d, J=18.54), 1.47 (2H, m), 1.98 (1H, m), 1.79 (1H, m), 1.98 (1H, t), 7.30 (1H, d), 7.75 (1H, t), 7.55 (1H, d), 2.91 (1H, d), 3.37 (1H, d).

* * * * *